US00RE34837E

United States Patent [19]

Iwanami et al.

[11] E Patent Number: Re. 34,837

[45] Reissued Date of Patent: Jan. 24, 1995

[54] FEEDS

[75] Inventors: Takefumi Iwanami, Kawasaki; Kiyoshi Maruta, Machida; Ichiya Murota, Sagamihara; Hiroshi Miyazaki, Tokyo, all of Japan

[73] Assignee: The Calpis Food Industry Co., Ltd, Tokyo, Japan

[21] Appl. No.: 69,200

[22] Filed: May 28, 1993

Related U.S. Patent Documents

Reissue of:

[64] Patent No.: 4,919,936
Issued: Apr. 24, 1990
Appl. No.: 44,477
Filed: May 1, 1987

[51] Int. Cl.[6] ..... A23K 1/17; C12R 1/07

[52] U.S. Cl. ..... 424/442; 426/61; 426/623; 426/630; 426/635; 426/636; 435/252.5; 435/839

[58] Field of Search ..... 435/252.5, 839; 426/61, 426/623, 630, 635, 636; 424/442

[56] References Cited

U.S. PATENT DOCUMENTS 2,132,621 10/1938 Horvath ..... 426/18
4,105,804 8/1978 Terui et al. ..... 435/839

FOREIGN PATENT DOCUMENTS 59-128334 7/1984 Japan .
60-75238 4/1985 Japan .
1069400 5/1967 United Kingdom .

OTHER PUBLICATIONS

Sneath et al., *Bergey's Manual of Systematic Bacteriology*, vol. 2, Williams & Wilkins, 1986, pp. 1105, 1108, 1120 and 1122.

Chemical Abstracts, vol. 106: No. 9, Mar. 1987, p. 493, abstract 65874q.

Chemical Abstracts, vol. 98: No. 3, Jan. 17, 1983, abstract 15283s.

Chemical Abstracts, vol. 99: No. 9, Aug. 29, 1983, abstract No, 68697g.

Chemical Abstracts, vol. 96: No. 5, Feb. 1, 1982, abstract No. 33132e.

The Journal of Immunology, "Purification to Apparent Homogeneity of Murine Interleukin 1", vol. 126, No. 3, pp. 834–837, Mar. 1981.

Chemical Abstracts, vol. 99: No. 13, Sep. 26, 1983, abstract No. 103513t.

Chemical Abstracts, vol. 99: No. 11, Sep. 12, 1983, abstract No. 85766w.

Chemical Abstracts, vol. 98: No. 17, Apr. 25, 1983, abstact No. 141398w.

Proc. Natl. Acad. Sci., "Leukemia cell lines can replace monocytes for mitogen-induced T-lymphocyte responses": This accessory function is dependent upon their differentiation stage:, vol. 80, pp. 6028–6031, Oct. 1983.

*Primary Examiner*—Marian Knode
*Assistant Examiner*—Maria L. Osoteo
*Attorney, Agent, or Firm*—Darby & Darby

[57] ABSTRACT

By giving mammals, fowls, fish, etc. feeds containing Bacillus subtilis C-3102 FERM BP-1096), an excellent body weight gain and feed efficiency can be obtained.

2 Claims, No Drawings

FEEDS

Matter enclosed in heavy brackets [ ] appears in the original patent but forms no part of this reissue specification; matter printed in italics indicates the additions made by reissue.

FIELD OF INDUSTRIAL APPLICATION

The present invention relates to feeds containing Bacillus subtilis C-3102.

Bacillus subtilis C3102 in accordance with the present invention exhibits the remarkable effects of increasing weight and improving feed efficiency, when it is given to animals, such as mammals, fowls and fishes as a feedstuff.

Accordingly, the present invention plays an important role not only in the art of microorganisms but also in the arts of livestock industry and fisheries.

PRIOR ART

Animal meat is very important as a foodstuff or a feedstuff. Accordingly, it has been strongly desired in the industrial world to efficiently raise economic animals.

For this reason, extensive investigations have been made from old on a formulation ratio of main ingredients which are inexpensive and have good nutritional balance, vitamins and minerals as trace components, and the like. Further a variety of probiotics (live bacterial agents) have been examined and the effects thereof have been noted to a certain extent but are yet unsatisfactory.

SUMMARY OF THE INVENTION

The present invention relates to feeds containing Bacillus subtilis C3102; such bacteria have been neither found heretofore nor has it been known that this new strain can show an excellent effect as a probiotic.

PROBLEM TO BE SOLVED BY THE INVENTION

As described above, it is the actual situation that any satisfactory probiotic having excellent safety and having a weight-increasing effect is unknown in the current feed industry and microorganism industry.

MEANS FOR SOLVING THE PLROBLEM

In view of the circumstances described above, the present invention has been made and from the viewpoint that there is no alternative other than finding hitherto unknown, new bacteria in order to solve the problem described above, various screening tests have been repeated. As a result, a novel strain belonging to the genus Bacillus has been discovered and has been named Bacillus subtilis C-3102.

A useful and novel finding has been noted that when this Bacillus subtilis C-3102 is incorporated and contained in animal feeds, it can accelerate the gain of weight in animals and at the same time, can improve feed efficiency; and as a result of further investigations, the present invention has been accomplished.

Namely, the present invention relates to probiotics comprising Bacillus subtilis C-3102 and relates to feeds containing Bacillus subtilis C-3102.

The strain used in the present invention is Bacillus subtilis C-3102 newly isolated from the natural world by the present inventors.

Bacillus subtilis C-3102 has been deposited in Fermentation Research Institute, Agency of Industrial Science and Technology, Japan, under FERM BP-1096. Bacteriological properties of this strain are as follows.

A. Morphological Properties (1) Cells: rods having a width of 0.6 to 1.0 μm and a length of 1.5 to 2.0 82 m.
(2) Gram-positive
(3) Spores: oval
(4) Mobility: positive
(5) Aerobic

B. Growth Conditions in Various Media (1) Nutrient agar: excellent
(2) Anaerobic glucose bouillon: −
(3) 7% NaCl: +

C. Physiological Properties (1) Growth at 50° C.; +
(2) Growth at pH 5.7: +
(3) Utilization of citrate: +
(4) Acid production from carbohydrates arabinose, glucose, xylose, mannitol: +
(5) VP reaction: +
(6) Hydrolysis of starch: +
(7) Reduction of nitrate: +
(8) Production of indole: −
(9) Liquefaction of gelatin: +
(10) Decomposition of casein: +
(11) Film formation of liquid medium: +
(12) Coagulation of milk: −
(13) Peptonization of milk: +
(14) Catalase: +

Next, a method for culturing Bacillus subtilis C-3102 of the present invention will be described.

As media, there can be widely used media ordinarily used for culturing microorganisms containing carbon sources, nitrogen sources, inorganic matters, vitamins, amino acids, etc. The carbon source can be any carbon compounds which are assimilable and, for example, glucose, sucrose, starch, molasses, etc. can be employed. The nitrogen source can be any nitrogen compounds which are utilizable and, for example, peptone, meat extract, casein acid hydrolysate, ammonium sulfate, etc. can be employed. In addition, phosphates, salts of metals such as magnesium, sodium, potassium, calcium, iron, manganese, etc.; vitamins, amino acids, defoaming agents, surfactants, etc. can also be used, depending upon necessity.

As the media, both liquid media and solid media can be used and incubation under aerobic conditions is appropriate.

Incubation can be suitably effected at an initial pH of the medium is pH of 5 to 9, preferably 6 to 8, at culturing temperatures at 20° to 50° C., preferably 35° to 40° C. and for a culturing time period of 12 hours to 7 days.

The thus obtained culture can be used as it is or as washed bacteria. Further the culture or bacteria can also be used as it is or after additives (carriers innocious to animals) are added thereto followed by drying or preparations thereof are produced. The probiotics of the present invention include these forms for use, which comprises Bacillus subtilis C-3102. It is sufficient that Bacillus subtilis C-3102 be incorporated in an amount of 10 to $10^{12}$ cells, preferably $10^4$ to $10^8$ cells, per 1 g of a feed but the amount is not limited only to such a range.

When the feed containing this bacteria is given to animals, a great weight-increasing effect can be obtained and feed conversion can also be greatly improved.

Moreover, the feed containing the bacteria is extremely effective for a variety of animals, in addition to mammals such as cows, pigs, horses, sheep, etc., various fowls such as chicken, quails, etc., and fishes. Furthermore, the feed is also useful for various pet animals such as dogs, cats, goldfishes, canaries, etc.

Hereafter preparation examples of the bacteria and reference examples showing fatting tests using the obtained probiotic will be described in detail.

PREPARATION EXAMPLE 1

Medium obtained by dissolving 400 g of soybean peptone, 10 g of dibasic potassium phosphate and 200 g of molasses in 60 liters of tap water and adjusting pH to 7.5 with 1N sodium hydroxide solution was charged in a jar fermenter and sterilized at 121° C. for 15 minutes. A culture solution of Bacillus subtilis C-b 3102, FERM BP-1096, which had been previously subjected to preliminary incubation, was inoculated thereinto followed by spinner culture under aeration at 37° C. for 40 hours.

The thus obtained culture solution was centrifuged to collect the cells. After drying, the cells were incorporated in skim milk powder to give 10 kg of a probiotic of Bacillus subtilis C-3102. The viable count contained in this probiotic was $1\times10^3$ cells/g.

PREPARATION EXAMPLE 2

To 5 kg of soybean oil meal granules (Fujinic Ace 500, manufactured by Fuji Purina Protein Co., Ltd.) was added 5 kg of tap water followed by sterilization at 121° C. for 120 minutes. A culture solution of Bacillus subtilis C-3102, FERM BP-1096, which had been previously subjected to preliminary incubation, was inoculated thereinto followed by culture at 37° C. for 40 hours.

The thus obtained culture solution was dried and reduced into powder. The powder was incorporated in calcium carbonate to give 4 kg of a probiotic of Bacillus subrilis C-3102. The viable count contained in this probiotic was $1\times10^{10}$ cells/g.

EXAMPLE 1

Male ICR mice of 6 age in weeks were divided into 2 groups (test gr. and control gr.) of 10 each and the feeds having the compositions as shown in Table 1 were given to the respective groups to conduct growth test. The probiotic obtained in Preparation Example 1 by incorporating into skim milk powder was used. The viable count in the feed in which the probiotic was added was $1\times10^6$ cells/g. The results are as shown in Table 2.

TABLE 1

| | (unit: wt %) | |
|---|---|---|
| | Invention | Control |
| CE-2(feed for mouse, manufactured by CLEA JAPAN, INC. | 99.9 | 99.9 |
| Skim milk powder | — | 0.1 |
| Probiotic of the present invention | 0.1 | — |

TABLE 2

| | Invention | Control |
|---|---|---|
| Feeding period (days) | 19 | 19 |
| Mean body weight at start (g) | 29.0 | 29.0 |
| Mean body weight at end (g) | 35.2 | 33.6 |
| Mean body weight gain (g) | 6.2 | 4.6 |
| [Body weight gain index] | [135] | [100] |
| Mean feed intake (g) | 109.2 | 103.0 |
| Feed conversion ratio | 17.6 | 22.4 |

As shown in Table 2, it is understood that by feeding the formula feed added with the probiotic of the present invention, an outstanding body weight-increasing effect was obtained and at the same time, the feed conversion ratio was also improved.

EXAMPLE 2

Piglets of 3 to 4 weeks were divided into 2 groups (test gr. and control gr.) of 6 each and the feeds having the compositions as shown in Table 3 were given to the respective groups to conduct growth test. The probiotic obtained in Preparation Example 2 by incorporating into calcium carbonate was used. The viable count in the feed in which the probiotic was added was $1\times10^6$ cells/g. The results are as shown in Table 4.

TABLE 3

| | (unit: wt %) | |
|---|---|---|
| | Invention | Control |
| Bakery waste (PANBIS, manufactured by Koike-Shoten Co.) | 7 | 37 |
| Skim milk powder | 35.99 | 35.99 |
| Feed which has adsorbed soybean extract (BITAZE 8, manufactured by Enaze Sangyo Co., Ltd.) | 11 | 11 |
| Glucose | 6 | 6 |
| Dehulled soybean powder (PAFESU 109, manufactured by Kikkoman Co., Ltd.) | 3 | 3 |
| Vitamins, minerals and other additives | 7 | 7 |
| Calcium carbonate | — | 0.01 |
| Probiotic of the present invention | 0.01 | — |

TABLE 4

| | Invention | Control |
|---|---|---|
| Feeding period (days) | 21 | 21 |
| Mean body weight at start (kg) | 6.1 | 6.1 |
| Mean body weight at end (kg) | 13.9 | 13.2 |
| Mean body weight gain (kg) | 7.8 | 7.1 |
| [Body weight gain index] | [110] | [100] |
| Mean feed intake (kg) | 67.9 | 67.3 |
| Feed conversion ratio | 1.45 | 1.58 |
| Observation of feces (ponts: cf. Note) | 19 | 54 |

Note: Total points of each group when normal feces, soft feces, diarrhea and watery feces were designated 0, 1, 2 and 3 points, respectively.

As shown in Table 4, it is understood that by feeding the formula feed added with the probiotic of the present invention, an outstanding body weight-increasing effect was obtained and at the same time, the feed conversion ratio was also improved, and further that the occurrence of diarrhea and soft feces was greatly reduced.

EXAMPLE 3

Broilers of 2 to 3 age in days were divided into 2 groups (test gr. and control gr.) of 30 each (15 females and 15 males) and the feeds having the compositions as shown in Table 5 were given to the respective groups to conduct growth test.

The probiotic obtained in Preparation Example 1 by incorporating into skim milk powder was used. The viable count in the feed in which the probiotic was added was $1\times10^6$ cells/g. The results are as shown in Table 6.

TABLE 5

| | (unit: wt %) | |
|---|---|---|
| | Invention | Control |
| Commercial formula feeds for broilers for use in a former feeding period (20 days) and for use in a latter feeding period (36 days) (manufactured by Kumiai Feed Co.) | 99.9 | 99.9 |
| Skim milk powder | — | 0.1 |
| Probiotic of the present invention | 0.1 | — |

TABLE 6

| | Invention | Control |
|---|---|---|
| Feeding period (days) | 56 | 56 |
| Mean body weight at start (kg) | 40 | 40 |
| Mean body weight at end (kg) | 2159 | 2000 |
| Mean body weight gain (g) | 2110 | 1960 |
| [Body weight gain index] | [108] | [100] |
| Mean feed intake (kg) | 4642 | 4528 |
| Feed conversion ratio | 2.20 | 2.31 |

As shown in Table 6, it is understood that by feeding the formula feed added with the probiotic of the present invention, an outstanding body weight-increasing effect was obtained and at the present time, the feed conversion ratio was also improved.

EXAMPLE 4

Laying chickens were divided into 2 groups (test gr. and control gr.) of 30 each and the feeds having the compositions shown in Table 7 were given to the respective groups to conduct a test. The probiotic obtained in Preparation Example 1 by incorporating into skim milk powder was used. The viable count in the feed in which the probiotic was added was $1\times10^6$ cells/g. The results are as shown in Table 8.

TABLE 7

| | unit: wt % | |
|---|---|---|
| | Invention | Control |
| Commercial formula feed (Kumiai Feed Co.) | 99.9 | 99.9 |
| Skim milk Powder | — | 0.1 |
| Probiotic of the present invention | 0.1 | — |

TABLE 8

| | Invention | Control |
|---|---|---|
| Feeding period (days) | 28 | 28 |
| Total number of laid eggs | 712 | 672 |
| [Laid-egg number index] | [106] | [100] |
| Mean egg weight (g) | 60.2 | 59.2 |
| [Egg weight index] | [102] | [100] |

As shown in Table 8, it is understood that by feeding the formula feed added with the probiotic of the present invention, the number of laid eggs increased and at the same time, the mean egg weight also increased.

EXAMPLE 5

Rainbow trout fry of approximately 14 g were divided into 2 groups (test gr. and control gr) of 30 each and the feeds having the compositions as shown in Table 9 were given to the respective groups to conduct a growth test. The probiotic obtained in Preparation Example 1 by incorporating into skim milk powder was used. The viable count in the feed in which the probiotic was added was $1\times10^6$ cells/g. The results are as shown in Table 10.

TABLE 9

| | (unit: wt %) | |
|---|---|---|
| | Invention | Control |
| Northern-sex fish meal | 55 | 55 |
| α-Starch | 20 | 20 |
| Dextrin | 5 | 5 |
| Oil mixture | 10 | 10 |
| Cellulose | 3 | 3 |
| Vitamins, minerals and other additives | 6.9 | 6.9 |
| Skim milk powder | — | 0.1 |
| Probiotic of the present invention | 0.1 | — |

TABLE 10

| | Invention | Control |
|---|---|---|
| Feeding period (days) | 45 | 45 |
| Mean body weight at start (g) | 14.3 | 14.0 |
| Mean body weight at end (g) | 39.6 | 37.6 |
| Mean body weight gain (g) | 25.3 | 23.6 |
| [Body weight gain index] | [107] | [100] |

As shown in Table 10, by feeding the formula feed added with the probiotic of the present invention, an outstanding body weight-increasing effect can be noted.

EXAMPLE 6

Calves of 1 week age after birth were divided into 2 groups (test gr. and control gr.) of 4 each and the feeds having the compositions as shown in Table 11 were given to the respective groups to conduct growth test. The probiotic obtained in Preparation Example 2 by incorporating into calcium carbonate was used. The viable count in the feed in which the probiotic was added was $1\times10^6$ cells/g. Upon performing the test, 1 part by weight of the feed was dissolved and dispersed in 7 parts by weight of hot water, which was then fed to the calves. The results are as shown in Table 12.

TABLE 11

| | (unit: wt %) | |
|---|---|---|
| | Invention | Control |
| Skim milk powder | 70 | 70 |
| Whey | 10 | 10 |
| Beef tallow | 12.49 | 12.49 |
| Lecithin | 0.5 | 0.5 |
| Vitamins, minerals and other additives | 7 | 7 |
| Calcium carbonate | — | 0.01 |
| Probiotic of the present invention | 0.01 | — |

TABLE 12

| | Invention | Control |
|---|---|---|
| Feeding period (days) | 28 | 28 |
| Mean body weight at start (kg) | 43.7 | 43.9 |
| Mean body weight at end (kg) | 75.3 | 73.9 |
| Mean body weight gain (kg) | 31.6 | 30 |
| [Body weight gain index] | [105] | [100] |
| Mean feed intake (kg) | 44.9 | 44.1 |
| Feed conversion ratio | 1.42 | 1.47 |
| Observation of feces | 29 | 45 |

TABLE 12-continued

| | Invention | Control |
|---|---|---|
| (ponts: cf. Note) | | |

Note: Total points of each group when normal feces, soft feces, diarrhea and watery feces were designated 0, 1, 2 and 3 points, respectively. As shown in Table 12, it is understood that by feeding the formula feed added with the probiotic of the present invention, an outstanding body weight-increasing effect was obtained and at the same time, the feed conversion ratio was also improved, and further that the occurrence of diarrhea and soft feces was greatly reduced.

What is claimed is:

1. A method for increasing the weight gain in animals comprising feeding to said animals a food which is supplemented with an amount effective to increase the weight of a probiotic comprising a carrier and Bacillus subtilis C-3102 (FERM PB-1096).

2. A method for increasing the weight of eggs comprising feeding to laying hens a food which is supplemented with an effective amount to increase the weight of said eggs of a probiotic comprising a carrier and Bacillus subtilis C-3102 (FERM BP-1096).

* * * * *